(12) United States Patent
Smith

(10) Patent No.: US 9,788,860 B2
(45) Date of Patent: Oct. 17, 2017

(54) PEDICURE ASSEMBLY

(71) Applicant: Learrel Smith, Rancho Cordova, CA (US)

(72) Inventor: Learrel Smith, Rancho Cordova, CA (US)

( * ) Notice: Subject to any disclaimer, the term of this patent is extended or adjusted under 35 U.S.C. 154(b) by 178 days.

(21) Appl. No.: 14/656,897

(22) Filed: Mar. 13, 2015

(65) Prior Publication Data

US 2016/0262797 A1    Sep. 15, 2016

(51) Int. Cl.
*A45D 29/05* (2006.01)
*A61B 17/54* (2006.01)
*A61B 17/00* (2006.01)
*A61B 17/32* (2006.01)

(52) U.S. Cl.
CPC .... *A61B 17/54* (2013.01); *A61B 2017/00398* (2013.01); *A61B 2017/00734* (2013.01); *A61B 2017/00761* (2013.01); *A61B 2017/320004* (2013.01)

(58) Field of Classification Search
CPC ........ A45D 29/00; A45D 29/05; A45D 29/14; A45D 29/11; A45D 29/12; A45D 29/04; A45D 29/007; A61B 17/54; A61B 2017/00398; A61B 2017/00734; A61B 2017/00761; A61B 2017/320004
See application file for complete search history.

(56) References Cited

U.S. PATENT DOCUMENTS

| | | | | | |
|---|---|---|---|---|---|
| 2,056,379 | A | * | 10/1936 | Acocella | A45D 29/14 132/73.6 |
| 2,597,525 | A | * | 5/1952 | Kessler | A45D 29/14 132/75.8 |
| 2,861,578 | A | * | 11/1958 | Thompson | A45D 29/05 132/73.6 |
| 4,440,182 | A | * | 4/1984 | Holm | A45D 29/14 132/73.6 |
| 6,178,970 | B1 | | 1/2001 | Purifoy et al. | |
| 6,523,546 | B2 | | 2/2003 | Jo | |
| 7,581,545 | B1 | | 9/2009 | Moldawski et al. | |
| D684,723 | S | | 6/2013 | Tsai | |
| 2002/0107527 | A1 | * | 8/2002 | Burres | A45D 29/14 606/131 |
| 2006/0000483 | A1 | * | 1/2006 | O'Dwyer | A45D 29/007 132/74.5 |
| 2006/0122631 | A1 | | 6/2006 | Kertz | |
| 2006/0137703 | A1 | * | 6/2006 | Kling | A45D 29/05 132/73.6 |
| 2006/0272664 | A1 | | 12/2006 | O'Dwyer | |
| 2010/0000557 | A1 | * | 1/2010 | Keene | A45D 29/14 132/73.6 |
| 2011/0226268 | A1 | * | 9/2011 | Filonczuk | A45D 29/05 132/73.6 |
| 2015/0150352 | A1 | * | 6/2015 | Yiu | A45D 29/05 132/75.8 |

FOREIGN PATENT DOCUMENTS

| | | | |
|---|---|---|---|
| DE | 3903828 A1 * | 8/1990 | ............ A45D 29/05 |
| WO | WO2009148729 | 12/2009 | |

* cited by examiner

*Primary Examiner* — Robyn Doan

(57) ABSTRACT

A pedicure assembly includes a housing that has a handle portion and a motor portion. A buffing unit is attached to the housing and the buffing unit abrasively removes calluses. The buffing unit comprises a drive and a head. An abrasive pad is attached to the head and the abrasive pad may be positioned to abut the callus thereby facilitating the abrasive pad to abrade and eliminate the callus.

1 Claim, 5 Drawing Sheets

PEDICURE ASSEMBLY

BACKGROUND OF THE DISCLOSURE

Field of the Disclosure

The disclosure relates to pedicure devices and more particularly pertains to a new pedicure device for removing calluses.

SUMMARY OF THE DISCLOSURE

An embodiment of the disclosure meets the needs presented above by generally comprising a housing that has a handle portion and a motor portion. A buffing unit is attached to the housing and the buffing unit abrasively removes calluses. The buffing unit comprises a drive and a head. An abrasive pad is attached to the head and the abrasive pad may be positioned to abut the callus thereby facilitating the abrasive pad to abrade and eliminate the callus.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF THE DRAWINGS

The disclosure will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
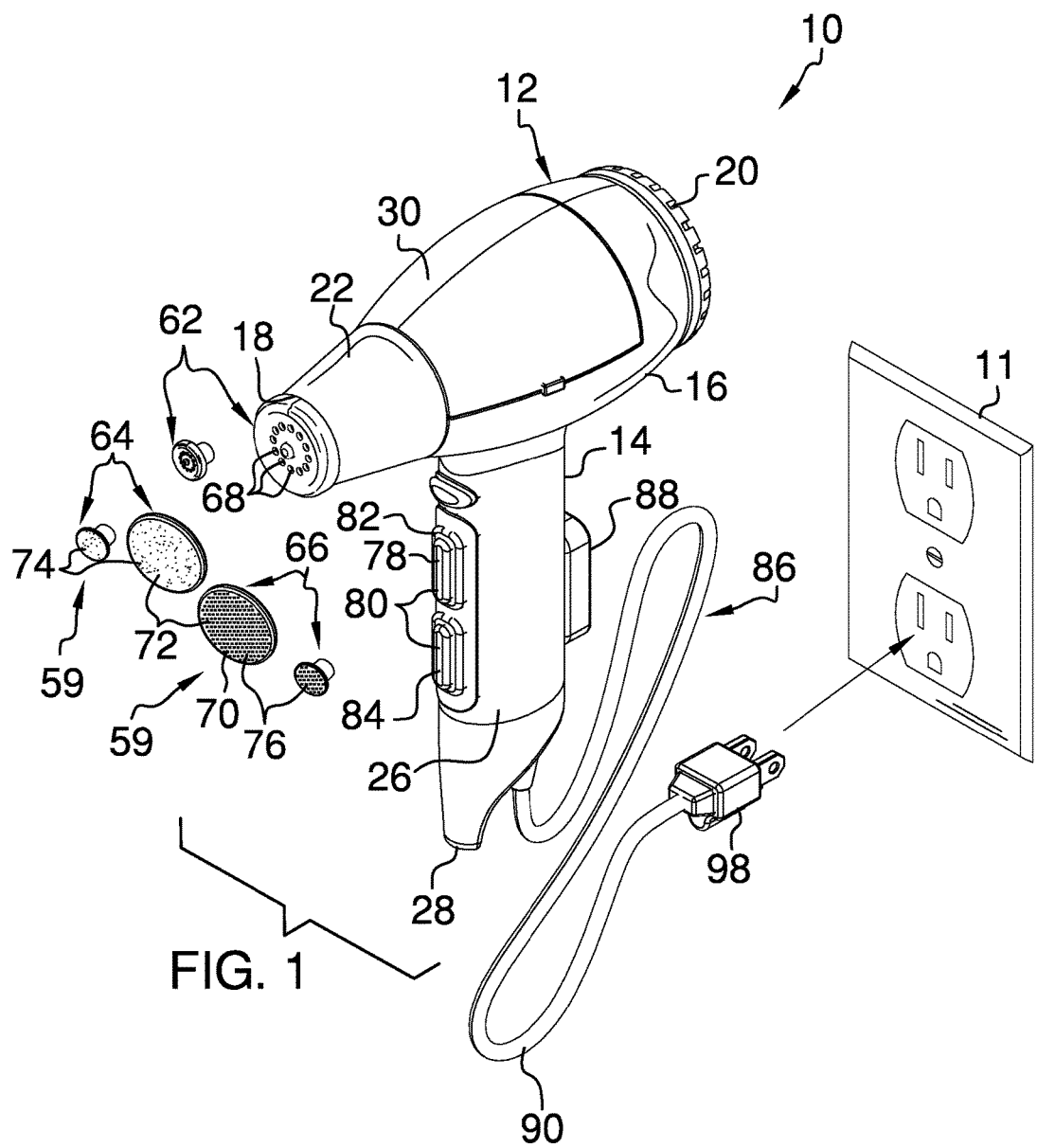
FIG. 1 is a kit view of a pedicure assembly according to an embodiment of the disclosure.
Figure 2:
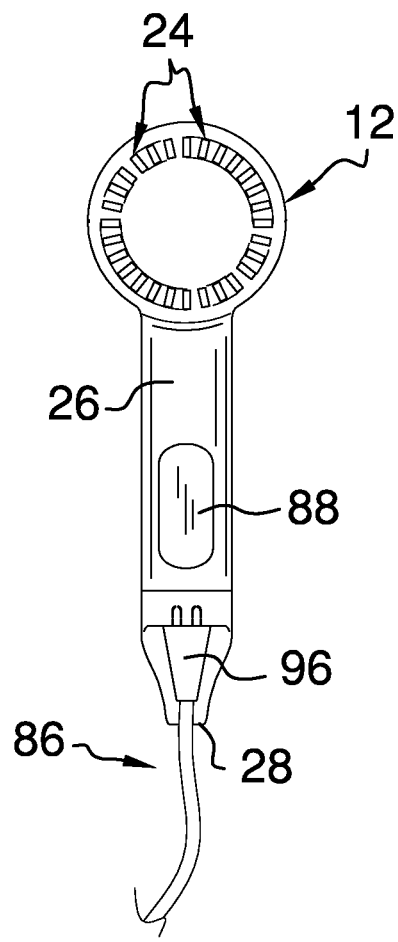
FIG. 2 is a back view of an embodiment of the disclosure.
Figure 3:
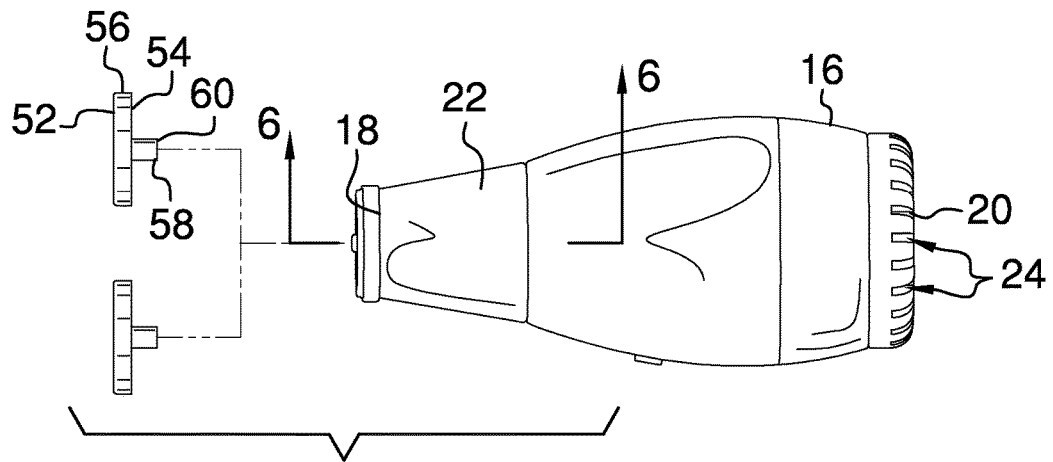
FIG. 3 is a top view of an embodiment of the disclosure.
Figure 4:
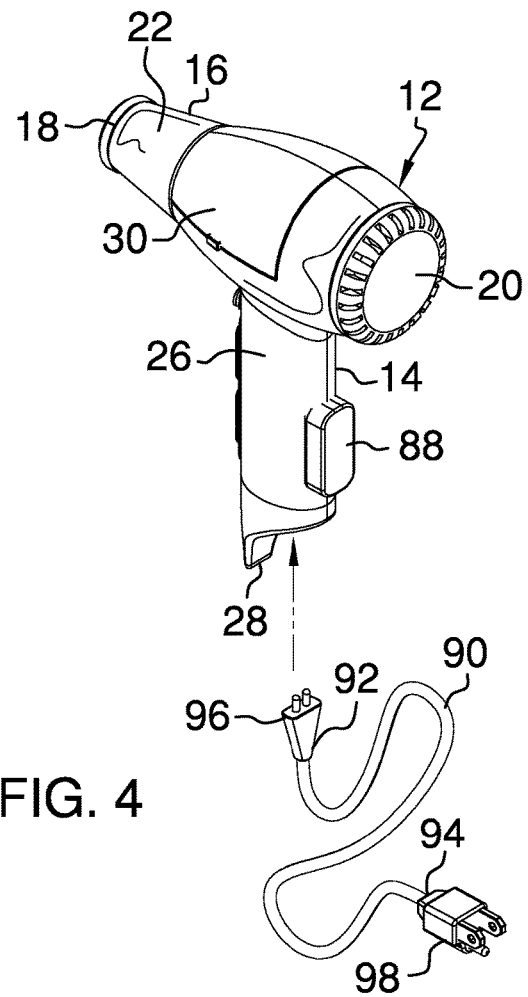
FIG. 4 is a perspective view of an embodiment of the disclosure.
Figure 5:
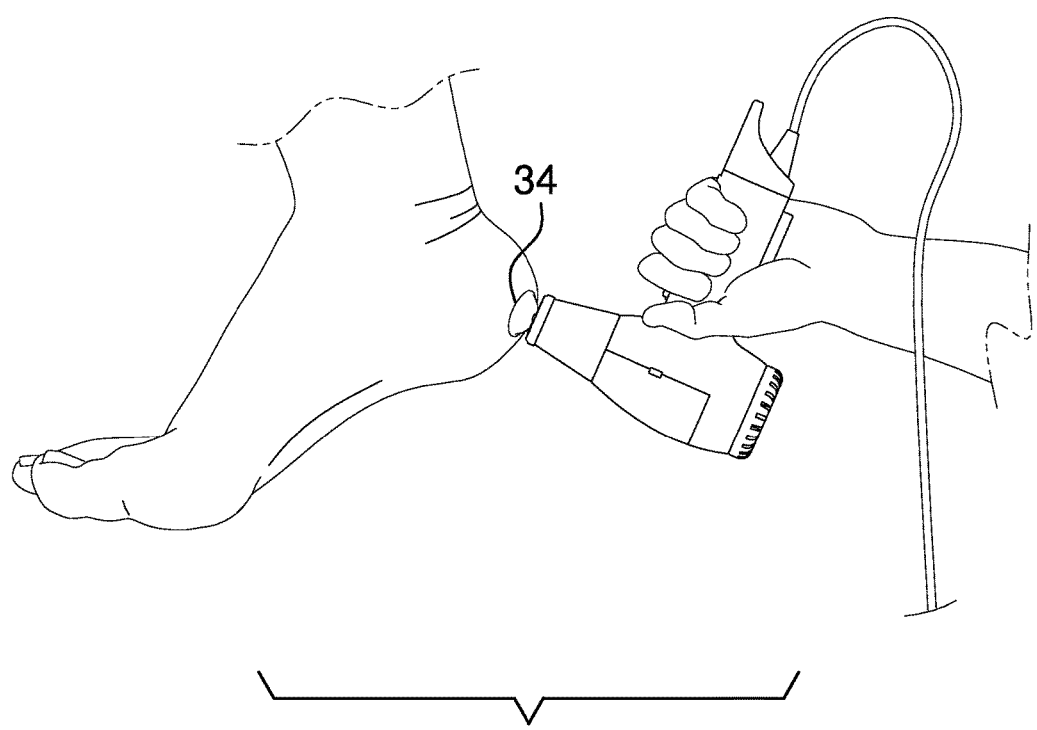
FIG. 5 is a perspective in-use view of an embodiment of the disclosure.
Figure 6:
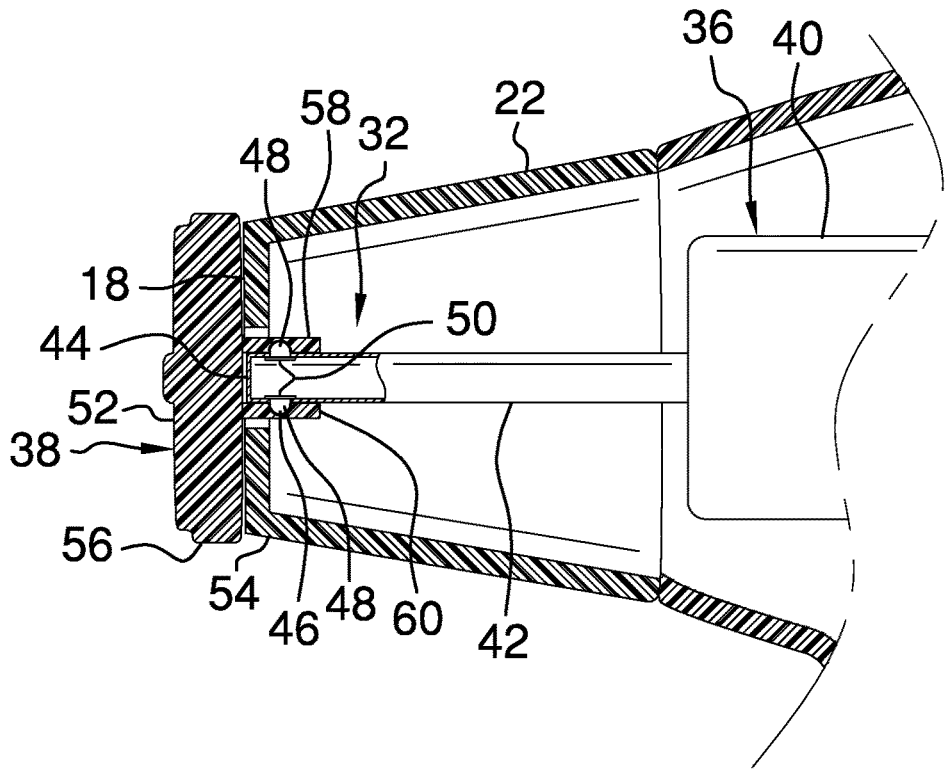
FIG. 6 is a cross sectional view taken along line 6-6 of FIG. 3 of an embodiment of the disclosure.
Figure 7:
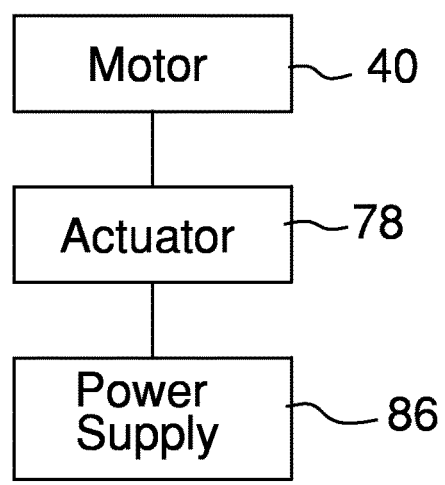
FIG. 7 is a schematic view of an embodiment of the disclosure.

With reference now to the drawings, and in particular to FIGS. 1 through 7 thereof, a new pedicure device embodying the principles and concepts of an embodiment of the disclosure and generally designated by the reference numeral 10 will be described.

As best illustrated in FIGS. 1 through 7, the pedicure assembly 10 generally comprises a housing 12 that has a handle portion 14 and a motor portion 16. The motor portion 16 has a front end 18, a back end 20 and a perimeter wall 22 extending between the front end 18 and the back end 20. The back end 20 has a plurality of vents 24 extending therethrough and the perimeter wall 22 is curved such that the motor portion 16 has a cylindrical shape. The front end 18 has a diameter that is less than a diameter of the back end 20. The handle portion 14 has a peripheral wall 26 and the peripheral wall 26 extends downwardly from the motor portion 16. The handle portion 14 has a distal end 28 with respect to the motor portion 16 and the handle portion 14 may be gripped.

A door 30 is hingedly attached to the motor portion 16. The door 30 is positionable in an open position to access and interior of the motor portion 16 and the door 30 is positionable in a closed position to cover the interior of the motor portion 16. A buffing unit 32 is attached to the housing 12 and the buffing unit 32 abrasively removes calluses 34. The buffing unit 32 comprises a drive 36 and a head 38.

The drive 36 includes a motor 40 positioned within the motor portion 16. The motor 40 may be an electrical motor or the like. A shaft 42 is coupled to the motor 40 such that the motor 40 rotates the shaft 42 when the motor 40 is turned on. The shaft 42 has a distal end 44 with respect to the motor 40 and the distal end 44 of the shaft 42 extends through the front end 18 of the motor portion 16. The shaft 42 includes a retainer 46 positioned adjacent to the distal end 44 of the shaft 42. The retainer 46 comprises a pair of balls 48 movably coupled to the shaft 42 and a biasing member 50 positioned within the shaft 42. The biasing member 50 biases each of the balls 48 outwardly from the shaft 42.

The head 38 has a front surface 52, a back surface 54 and a peripheral edge 56 extending between the front surface 52 and the back surface 54. The head 38 includes a coupler 58 attached to and extending away from the back surface 54. The coupler 58 has a distal end 60 with respect to the back surface 54 and the distal end 60 of the coupler 58 is open. The distal end 60 of the coupler 58 insertably receives the distal end 44 of the shaft 42. The retainer 46 engages the coupler 58 thereby facilitating the head 38 to be releasably retained on the shaft 42. The retainer 46 prevents the head 38 from being removed from the shaft 42 through centrifugal force.

The head 38 may be one of a plurality of sets of heads 59 and the plurality of sets of heads 59 may include a set of cutting heads 62, a set of abrading heads 64 and a set of polishing heads 66. Each of the set of cutting heads 62 may have a plurality of blades 68 attached to the front surface 52 to remove large amounts of the callus 34. Additionally, each of the set of cutting heads 62, the set of abrading heads 64 and the set of polishing heads 66 may come in plurality of sizes.

An abrasive pad 70 attached to the front surface 52 of each of the abrading heads 64 and the polishing heads 66 and the abrasive pad 70 is positioned to abut the callus 34. The motor 40 rotates the head 38 wherein the abrasive pad 70 abrades and eliminates the callus 34. The abrasive pad 70 may be one of a plurality of abrasive pads 72 and the plurality of abrasive pads 72 may include a set of coarse pads 74 and a set of smooth pads 76. The coarse pads 74 are positioned on the set of abrading heads 64 and the smooth pads 76 are positioned on the set of polishing heads 66. The abrading heads 64 are used to abrade the callus 34 and the polishing heads 66 are used to smooth the area from which the callus 34 was removed.

An actuator 78 is attached to the handle portion 14. The actuator 78 is electrically coupled to the motor 40 such that actuator 78 selectively actuates and de-actuates the motor 40. The actuator 40 may be one of a pair of actuators 80 and the pair of actuators 80 may include a fast speed actuator 82 and a slow speed actuator 84. The fast speed actuator 82 actuates the motor 40 to a maximum rotational speed and the slow speed actuator 84 actuates the motor 40 to a minimum rotational speed.

A power supply 86 is attached to the handle portion 14 and the power supply 86 is electrically coupled to the actuator 78. The power supply 86 comprises at least one battery 88 attached to the peripheral wall 26 of the handle portion 14 and a cord 90 that has a first end 92 and a second end 94. The first end 92 has a first plug 96 electrically coupled thereto and the second end 94 has a second plug 98 electrically coupled thereto. The first plug 96 is removably attached to the distal end 28 of the handle portion 14 wherein the cord 90 is electrically coupled to the actuator 78. The second plug 98 may be electrically coupled to a power source 11. The cord 90 charges the battery 88 and supplies electrical power to the actuator 78.

In use, a selected one of the cutting heads 62, the abrading heads 64 and the polishing heads 66 is releasably coupled to the shaft 42. The selected head 38 is positioned to abut the callus 34 and the actuator 78 is engaged to rotate the head 38. The cutting head 62 is used to remove large amounts of the callus 34 and the abrading head 64 is used to remove small amounts of the callus 34. The polishing head 66 is used to smooth the area from which the callus 34 was removed.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. A pedicure assembly configured to remove excess skin from a user's extremities, said assembly comprising:
    a housing having a handle portion and a motor portion, said motor portion having a front end, a back end, and a perimeter wall extending between said front end and said back end, said back end having a plurality of vents extending therethrough, said perimeter wall being curved such that said motor portion has a cylindrical shape, said front end having a diameter being less than a diameter of said back end, said handle portion having a peripheral wall, said peripheral wall extending downwardly from said motor portion, said handle portion having a distal end with respect to said motor portion;
    a door hingedly attached to said motor portion, said door being positionable in an open position to access an interior of said motor portion, said door being positionable in a closed position to conceal said interior of said motor portion; and
    a buffing unit attached to said housing, said buffing unit being configured to abrasively remove calluses, said buffing unit comprising a drive and a head, said drive including
        a motor positioned within said motor portion,
        a shaft coupled to said motor such that said motor rotates said shaft when said motor is turned on, said shaft having a distal end with respect to said motor, said distal end extending through said front end of said motor portion, said shaft including a retainer positioned adjacent to said distal end, said retainer comprising
            a pair of balls movably coupled to said shaft, and
            a biasing member positioned within said shaft, said biasing member biasing each of said balls outwardly from said shaft
        an actuator attached to said handle portion, said actuator being electrically coupled to said motor such that actuator selectively actuates and de-actuates said motor,
        a power supply attached to said handle portion, said power supply being electrically coupled to said actuator, said power supply comprising
            at least one battery attached to said peripheral wall of said handle portion, and
            a cord having a first end and a second end, said first end having a first plug electrically coupled thereto, said second end having a second plug electrically coupled thereto, said first plug being removably attached to said distal end of said handle portion wherein said cord is electrically coupled to said actuator, said second plug being configured to be electrically coupled to a power source, said cord charging said battery and supplying electrical power to said actuator,
    said head having a front surface, a back surface and a peripheral edge extending between said front surface and said back surface, said head including a coupler attached to and extending away from said back surface, said coupler having a distal end with respect to said back surface, said distal end being open, said distal end of said coupler insertably receiving said distal end of said shaft, said retainer engaging said coupler thereby facilitating said head to be releasably retained on said shaft, said retainer preventing said head from being removed from said shaft through centrifugal force, and
    an abrasive pad attached to said front surface, said abrasive pad being configured to be positioned to abut the callus, said motor rotating said head when said actuator is engaged wherein said abrasive pad is configured to abrade and eliminate the callus.

\* \* \* \* \*